United States Patent [19]

Zenoni et al.

[11] Patent Number: 5,574,153

[45] Date of Patent: Nov. 12, 1996

[54] OXIME DERIVATIVES OF CEPHALOSPORANIC STRUCTURE

[75] Inventors: Maurizio Zenoni, Leffe; Mario Leone, Pioltello; Riccardo Colombo, Sesto San Giovanni, all of Italy

[73] Assignee: ACS Dobfar S.p.A., Milan, Italy

[21] Appl. No.: 281,170

[22] Filed: Jul. 27, 1994

[30] Foreign Application Priority Data

Aug. 9, 1993 [IT] Italy ................... MI93A1808

[51] Int. Cl.$^6$ ............ C07D 501/34; C07D 501/32; C07D 501/60
[52] U.S. Cl. .......... 540/222; 540/215; 540/217; 540/224; 540/225; 540/226; 540/227; 540/228; 540/229; 540/230
[58] Field of Search ................. 540/222, 215, 540/217, 224, 225, 226, 227, 228, 229, 230

[56] References Cited

U.S. PATENT DOCUMENTS 5,095,107  3/1992  Blanchard ................. 540/205
5,189,157  2/1993  Wei et al. ................. 540/222

OTHER PUBLICATIONS

Chemical Abstracts vol. 82 156339u (1979).
S. S. Ahmad–Junan et al, "Aryloxymethyl Radical Cyclizations Mimicking Biological C–C Bond Formation ot Methoxy Groups", J. Chem. Soc. Perkin Trans., 1, 1992, pp. 2321–2320.
Padwa et al, "Intramolecular Munchnone Cycloadditions: Preparation and Chemistry of the Intramolecular Dipolar Cycloadducts", J. Org. Chem, 1985, 50, 3816–3823.
Snider et al, "Intramolecular [2+2]Cycloadditions of Alkoxylketenes and Alkoxyketeniminium Salts", J. Org. Chem. 1985, 50, 5167–5176.
Brady et al, "Intramolecular [2+2]Cycloadditions of Ketene Iminium Salts to Carbon–Carbon Double Bonds", J. Org. Chem. 1987, 52, 2216–2220.
Kundig et al, "Low Temperature Grignard Reactions with Pure Mg Slurries. Trapping of Cyclopropylmethyl and Benzocyclobutenylmethyl Grignard Reagents with $CO_2$", Helvetica Chimica Acta, vol. 64, Fasc. 8 (1981) —Nr. 262, pp. 2606–2613.
Forrester et al, "Persulphate Oxidations. Part X[1]Heterocyclic Synthesis by Oxidation of ortho–Substituted Phenoxyacetic Acids", J. Chem. Soc., 18, (1974), 2161–2166.
H. Engelhard et al, "Versuche zur Verbesserung der Anfarbbarkeit von Acrylinitrilpolymerisaten", Ange. Makromol. Chem, 14, 1970, pp. 1–24.
Chemical Abstracts, vol. 53, No. 2, Jan. 25, 1960, Columbus, OH, USA, Abstract No. 10095i, N. Shigematsu, H. Kobayashi, "Allyl–or methoxy–substituted phenoxyacetic acid N,N–diethylamides and their pharmacological activities", & Tanabae Seiyaku Kenkyu Nempo, vol. 3, No. 2, 1958, pp. 33–37.
Chemical Abstracts, vol. 66, No. 21, May 22, 1967, Columbus, OH, USA, Abstract No. 94755n, S. Nikiforova, S.G. Melkanovitskaya, "Allylation of phenols and phenol ethers. VI, Allylation of resorcinol monomethyl ether in the presence of copper (I)", pp. 8857 & ZH. Org. Khim, vol. 3a Bi, 1m 1967, pp. 144–146.

*Primary Examiner*—John M. Ford
*Attorney, Agent, or Firm*—Oblon, Spivak, McClelland, Maier & Neustadt, P.C.

[57] ABSTRACT

The invention relates to oxime derivatives of cephalosporanic structure, possessing antibacterial activity.

7 Claims, No Drawings

OXIME DERIVATIVES OF CEPHALOSPORANIC STRUCTURE

This invention relates to oxime derivatives of cephalosporanic structure of formula (I) possessing antibacterial activity:

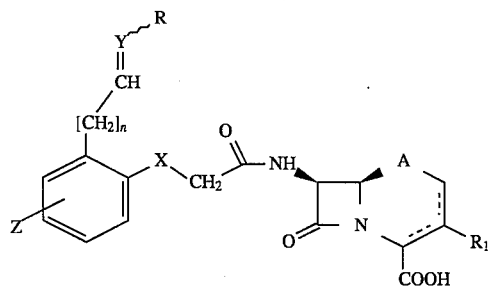

where the meanings of the various radicals and substituents are chosen from the following groups:

X=absent, —O—, —S—, —SO—, —SO$_2$—, —NH—

Y=—CH, N—

Z=—H, halogen, —OH, C$_1$-C$_5$ O-alkyl, —OCH$_2$CONH$_2$, —OCONH$_2$, —OSO$_2$NH$_2$, —OCH$_2$CN, —NH$_2$ either as such or substituted with C$_1$-C$_6$ alkyl radicals, —NHCOCH$_3$, —NHSO$_2$CH$_3$,

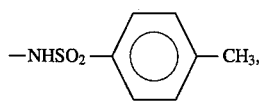

amides of C$_1$-C$_4$ linear acids, amides of benzene and toluene derivatives, —NO$_2$, —NO, —CHO, —CH$_2$OH, —COOH, —SH, —SOH, —SO$_2$H, —SO$_3$H, —S—alkyl where the alkyl residue is C$_1$-C$_3$, —CF$_3$ R: —H, —OH, C$_1$-C$_5$ —O—alkyl with the alkyl residue possibly containing halogens, acid functionalities either free or salified with alkaline or alkaline earth metals, basic functions such as —OCH$_2$CH$_2$NH$_2$, —OCH$_2$CH$_2$NH—CH$_3$, —OCH$_2$(o, m, p)-pyridinyl, —OCH$_2$CN, —OCH$_2$CONH$_2$, —OCH$_2$SO$_2$NH$_2$;

n=0 to 4

A=—S—, —O—, —CH$_2$—, —SO—, —SO$_2$—;

R$_1$=a structural group characteristic of cephalosporins, such as —Cl, —H, —OCH$_3$, —CH$_2$OCH$_2$NH$_3$, —CH$_2$OCH$_3$, —CH$_3$, —CH=CH—CH$_3$, —CF$_3$, —CO$_2$R$_2$, —SO$_2$R where R$_2$ is an alkyl or aryl radical

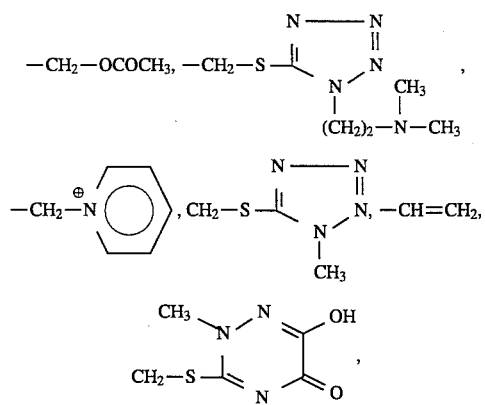

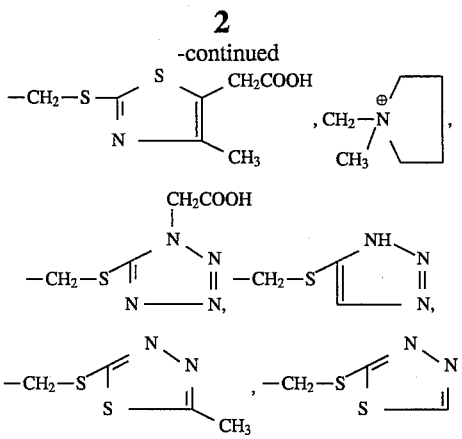

their pharmaceutically acceptable salts and their C$_6$ and C$_7$ epimers.

The oxime configuration can be either (E) or (Z), preferably (E), analogous with the structures already known in the specific literature of the sector. The configuration of the cephalosporanic nucleus is identical to already known structures.

The oxime derivatives of cephalosporanic structure according to the present invention possess the usual characteristics of cephalosporin analogues and are suitable for both oral and parenteral administration. In particular, in view of their spectrum of action, they are structurally comparable with both aminothiazole cephalosporins (cefotaxime, ceftizoxime, cefmenoxime, ceftriaxone, ceftazidime) and with those (cefuroxime) containing an oxime group able to increase their activity against β-lactamase producer bacteria. In addition because of the proximity of a substituent in the ortho position in the phenylacetic structure, there is similarity with ceforanide. Molecular mechanics studies have shown these analogies, which were then confirmed by studies effected in vitro on numerous bacterial strains.

These new molecules can be considered structurally to consist of two parts: "cephalosporanic nuclei" of formula (II)

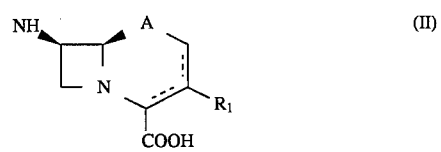

(all well known in the literature for their use in the main cephalosporanic derivatives of first, second, third or more recent generation), and an ortho-oxime group of phenyl-, phenylthio- or derivative, phenylamino or phenoxyacetic acids of formula (III):

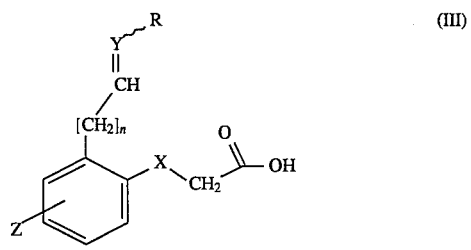

forming the side chain of the oxime derivatives of formula (I), the meanings of X, Y, Z, A, n, R and R$_1$ being as stated heretofore.

The ortho-oxime groups of formula (III) also form an aspect of the present invention.

The compounds of formula (I) can be easily prepared by reacting the compounds of formula (II) with those of formula (III).

Oxime synthesis is often diastereoselective and leads to the (E) isomer; the condensation reaction to give the (I) products is also diastereoselective. The configuration of the oxime of the products (III) or of the chiral centres in position 6 and 7 of the nuclei of formula (II) is not disturbed by the conditions used for their synthesis.

In order to further clarify the understanding of the invention, some oximes of formula (III) and their method of preparation will firstly be described in detail; some examples of the preparation of certain oxime derivatives (I) of cephalosporanic structure will then be given using the oximes (III) of the preceding examples.

PREPARATION OF REAGENTS (III)

A) Reagents of formula (III) in which X and Z are not present, n is 0 (zero), Y is N—, and R is as specified in the following Examples 1–6.

EXAMPLE 1 (R: —OH)

(E)-2-hydroxyiminomethyl-phenylacetic acid 2-formyl phenylacetic acid is used as starting material, prepared by the methods already known in the literature, such as DE-A-3836581 (acid CAS No. 1723-55-3, methyl ester CAS No. 63969-84-6, ethyl ether CAS No. 63969). The procedure used is that already known in the literature (for example VOGEL "CHIM. ORG. PRATICA" 2nd ed. page 1150).

5 g of hydroxylamine hydrochloride are added to 5 g of this acid (30 mmoles) in 50 ml of water and 20 g of sodium acetate and the system heated under reflux for 10 minutes, after which it is allowed to cool to 20° C. and is crystallized at pH 2.00. The product is filtered off and washed with water. It is dried under vacuum at 50° C.

Yield 4.9 g (27 mmoles) 91%. The configuration was determined by H NMR experiments (N.O.E): diastereoisomeric purity >98% (isomer E)

IR (KBr, $cm^{-1}$): 3250, 1760, 1600, 1550

NMR (solvent DMSO, istd TMS): 11.27 ppm (s, 1H), 8.27 ppm (s, 1H), 7.68/7.65 (m, 1H), 7.32/7.26 (m, 3H), 3.78 (s, 2H); outside the range there is a very broad signal attributable to the acid proton.

Melting point: 147° C.

EXAMPLE 2 (R: —OH)

(E)-2-methoxyiminomethyl-phenylacetic acid 1.8 g (10 mmoles) of 2-hydroxyiminomethyl-phenylacetic acid are reacted with 1.50 ml of iodomethane, 5 g of potassium carbonate and 10 mg of triethylbenzylammonium (TEBA) chloride in 20 ml of anhydrous acetonitrile. The system is left for 6 hours at +80° C. and overnight at ambient temperature.

The salts are filtered off and the residue containing the acid in the form of methylester is concentrated under vacuum. It is taken up in 50 ml of methylene chloride and saponified with 50 ml of 15% sodium hydroxide and 20 mg of tetrabutylammonium bromide at 20° C. for 12 hours. The organic phase is separated; the aqueous phase is acidified with HCl to pH 2.0. The acid obtained is recrystallized from water to obtain a single isomer.

Yield 0.46 g (2.4 mmoles) 24%. The configuration was determined by NMR (NOE) analysis.

IR (KBr, $cm^{-1}$): 3000/2500, 1780, 1608, 1600

NMR (solvent $CDCl_3$, istd TMS): 9.22 ppm (s, broad, 1H deuterable), 8.22 ppm (s, 1H), 7.58/7.52 ppm (m, 1H), 7.36/7.26 ppm (m, 3H), 3.94 ppm (s, 3H), 3.89 ppm (s, 2H)

Melting point: 120° C.

EXAMPLE 3 (R: 1,3-dithiolan-2-yl)

2-(1,3-dithiolan-2-yl)-phenylacetic acid 10 ml of 1,2-ethanedithiol (0.12 moles) and 115 ml of trifluoro diboro diethyletherate are added to a solution of 22 g (0.12 moles) of 2-formyl-phenylacetic acid methyl ester in 100 ml of methylene chloride at 20° C. The system is agitated at 20° C. for 48 hours. 152 ml of 5% sodium hydroxide are added, the phases are separated, the organic phase is dried over magnesium sulphate and the solvent is evaporated under vacuum at +30° C. In this manner 29.7 g of 2-(1,3-dithiolan-2-yl)-phenylacetic acid methyl ester are obtained in the form of a yellow liquid. This crude product is saponified without the need for further purification.

120 ml of 1N sodium hydroxide are added to a solution of 29.7 g of methyl ester in 300 ml of ethyl alcohol. The system is left under agitation at 20° C. for two hours after which 200 ml of ethyl acetate are added and the system acidified with 25 ml of 10% hydrochloric acid to pH 1. The phases are separated, the ethyl acetate is dried with magnesium sulphate and evaporated under vacuum at +40° C. to a residual 80 ml. It is filtered and dried under vacuum at +40° C. Yield 58.6%. This product is used only as intermediate for the preparation of condensation products with cephalosporanic nuclei. Deprotection and further oxime functionalization are conducted on the already condensed product.

IR (solution) 1705 $cm^{-1}$

NMR (solvent DMSO, istd TMS): 13 ppm (broad, 1H deuterable), 7.7 ppm (m, 1H), 7.3/7.1 ppm (m, 3H), 5.85 ppm (s, 1H), 3.72 ppm (s, 2H), 3.5 ppm (m, 2H), 3.3 (m, 2H)

Melting point: 150/154° C. with decomposition

EXAMPLE 4 (R: —$OCO_2COO$-t-But)

(E)-2-tert.butoxycarbonylmethyloxyiminomethyl phenylacetic acid 5.6 g (27.8 mmoles) of 2-hydroxyiminomethyl phenylacetic acid methyl ester are treated with 5 ml of tert-butyl-chloroacetate and 5.5 g of potassium carbonate by the previously described method. The reaction is conducted for 20 hours under reflux.

After (selective) saponification of the methyl ester by the already described procedure plus recrystallization, 3.75 g (12.5 mmoles) are obtained. Yield 45%. When subjected to potentiometric titration in methanol with tetrabutylammonium hydroxide, the product shows a single inflection. Stereochemistry and structure were confirmed by HNMR (N.O.E.) analysis.

IR (KBr, $cm^{-1}$): 3000/2980, 1740, 1610, 1600, 1500

NMR (DMSO): 13 (b, 1H), 8.51 (s, 1H), 7.6/7.0 (m, 4H), 4.6 (s, 2H), 3.78 (s, 2H), 1.43 (s, 9H)

Melting point: 115° C.

EXAMPLE 5 (R: —OCH₂CONH₂)

(E)-2-aminoccarbonylmethyleneoxyiminomethyl-phenylacetic acid

The procedure is identical to the preceding. Treatment with chloroacetamide is effected. From 2 g (9.9 mmoles) of methylester 0.585 g (2.5 mmoles) of product as a single isomer (NMR) are obtained after purification, yield 25%.

IR (KBr, cm$^{-1}$): 3500, 3250, 1710, 1650, 1580

NMR (DMSO): 13.1 (b, 1H), 8.55 (s, IH), 7.6/7.0 (m, 6H), 4.56 (s, 2H), 3.78 (s, 2H), 2H deuterable Melting point: 191° C.

EXAMPLE 6 (R: —OCONH₂)

(E)-2-aminocarbonyloxyiminomethyl-phenylacetic acid 5 g of methylester oxime (24 mmoles) are dissolved in 50 ml of tetrahydrofuran ay −30° C., and 2.3 ml (26 mmoles) of chlorosulphonyl isocyanate are added in 3 successive portions. The system is allowed to react for 2 hours at −20° C., 20 ml of water are added and the system left to hydrolyze at 0° C. for a further 2 hours. 100 ml of ethyl acetate are added, and the organic phase is washed twice with an aqueous sodium chloride solution. The rich phase is evaporated under vacuum. The crude reaction product is saponified with sodium hydroxide by the already described method. The crude product crystallized as acid (weight 4.7 g) is recrystallized from water to obtain 4.1 g (18 mmoles) of acid as a single isomer (E by NOE). Yield 75%.

IR (KBr, cm$^{-1}$): 3500/2700, 1740, 1600

NMR (DMSO): 13 (b, 1H), 8.58 (s, 1H), 7.6/6.8 (m, 6H), 3.78 (s, 2H)

Melting point: 203° C.

B) Reagents of formula (III) in which Z is not present, n is 0 (zero), X is —O—, Y is N— and R is as specified in Examples 7 to 10 as follows.

For these examples the starting material used is 2-formyl phenoxyacetic acid prepared by the methods described in the literature (for example on page 959 of Vogel—Chimica Organica Pratica). The procedure followed in each example is identical to that conducted on the phenylacetic derivative of the preceding Examples 1 to 6.

EXAMPLE 7 (R: —OCH₃)

(E) -2-methoxyiminomethyl phenoxyacetic acid

IR (KBr, cm$^{-1}$): 3050/2577, 1969, 1740, 1713, 1609, 1601, 1495

NMR (CDCl₃, ppm TMS): 8.17 (s, 1H), 7.43/7.35 (m, 2H), 7.1 (m, H), 6.9 (m, 1H), 4.7 (s, 2H), 3.99 (s, 3H)

Melting point: 122/124° C.

EXAMPLE 8 (R: —OCH₂COO-t-But)

(E) -2-tert.butoxycarbonylmethyleneoxyiminomethyl phenoxyacetic acid

IR (KBr, cm$^{-1}$): 3020, 2990, 2900, 1740, 1610, 1600

NMR (DMSO, TMS=0 ppm): 13.1 (b, 1H), 8.51 (s, 1H), 7.63 (m, 1H), 7.39 (m, 1m), 7.0 (m, 2H), 4.78 (s, 2H), 4.61 (s, 2H), 1.43 (s, 9H)

Melting point: 128/130° C.

EXAMPLE 9 (R: —OCH₂CONH₂)

(E)-2-aminocarbonylmethyleneoxyiminomethyl phenoxyacetic acid

IR (KBr, cm$^{-1}$): 3990, 3250, 2900/2600, 1710, 1650, 1585

NMR (DMSOd₆, TMS=0 ppm): 13.1 (b, 1H), 8.55 (s, 1H), 7.65 (m, 1H), 7.37 (m, 1H), 7.35 (b, 1H), 7.27 (b, 1H), 7.0 (m, 2H), 4.78 (s, 2H), 4.56 (s, 2H)

Melting point: 179/182° C.

EXAMPLE 10 (R: —OCH₂(2—PY))

(E)-2-(pyridin-2-ylmethyleneoxyiminomethyl)phenoxyacetic acid

IR (KBr, cm$^{-1}$): 3100, 2950, 1720, 1600, 1490

NMR (CDCl₃, TMS=0 ppm): 8.50 (m, 1H), 8.16 (s, 1H), 7.4/6.9 (m, 7H), 4.7 (s, 2H), 4.57 (s, 2H), 1H broad outside range deuterable Melting point: 191/193° C. with decomposition C) Reagents of formula (III) in which Z is not present, X is —O—, n is 1, Y and R are as specified in the following Examples 11 to 14.

EXAMPLE 11 (Y: —CH; R: —H)

1-(prop-2-enyl) phenoxyacetic-(2-allyl)phenoxyacetic acid

The starting material is 2-allylphenol and the procedure is similar to that already described.

33.5 g (250 mmoles) of 2-allylphenol are reacted with 45.9 g (275 mmoles) of ethyl bromoacetate, 38 g (275 mmoles) of potassium carbonate and 300 mg of TEBA in 300 ml of acetonitrile and 10 ml of water. The reaction is conducted under reflux (80° C.) for 8 hours, until the starting product completely disappears. When synthesis is complete the solvent is distilled off under vacuum. The residue is taken up in 200 ml of methylene chloride and 200 ml of water containing 5% of concentrated hydrochloric acid. The rich organic phase is washed twice with water (200 ml each) and concentrated under vacuum until an oily residue (d 1.07) is obtained. 53 g of a nearly pure (>97%) product in the form of ethyl ester is obtained, the yield being 96%. The crude product is saponified by the method already described.

After crystallization, 43 g (224 mmoles) of free acid are obtained in the form of a white crystalline powder. Yield 89%.

IR (KBr, cm$^{-1}$): 3030/2500, 1740, 1700, 1600, 1580

NMR (DMSOd₆, TMS=0 ppm): 7.17/7.10 (m, 2H), 6.9/6.8 (m, 2H), 5.97 (m, 1H), 5.1 (m, 2H), 3.33 (d, 2H)

Melting point: 147° C.

EXAMPLE 12 (Y: N—; R: —OH)

(E,Z)-2-(2-hydroxyiminoethyl)-phenoxyacetic acid 10 g (52 mmoles) of 2-allylphenoxyacetic acid are dissolved in 50 ml of isopropanol land 200 ml of methylene chloride. The solution is cooled to −70° C. and subjected to ozonolysis. After appearance of the characteristic bluish colour (about 1 hour), the ozone flow is interrupted and nitrogen is bubbled through for 30 minutes. The ozonides are quenched with 6 ml (80 mmoles) of methyl sulphide. The system is kept under agitation overnight at 20° C. The solution is concentrated under vacuum and taken up with 200 ml of a 15% solution of dipotassium phosphate. The insoluble part is filtered off. The aqueous phase is decolorized with carbon and acidified with concentrated hydrochloric acid to pH 2 in the presence of 200 ml of ethyl acetate. The phases are separated and the organic phase is washed twice with water. It is dried over magnesium sulphate and concentrated under vacuum. 4.2 g of an amorphous solid are obtained. Potentiometric titration with sodium hydroxide shows a purity of 95%, and I.R. analysis confirms the presence of the aldehyde group (1750 cm$^{-1}$, 1720 cm$^{-1}$). The crude product as such is treated, by the previously described procedure, with hydroxylamine hydrochloride to give the corresponding oxime. After crystallization, 4 g of product are obtained as a white crystalline solid (19 mmoles). The product is a mixture of isomers (syn, anti) which cannot be separated by fractional crystallization.

IR (KBr, cm$^{-1}$): 3500/2900, 1715, 1500

NMR (DMSO, istd TMS=0 ppm): 11.25 (s, 1H), 8.37 (t, 1H), 7.5/6.9 (4H, m), 4.7 (s, 2H), 3.8 (d, 2H), 13 pp (broad, 1H)

Melting point: 110° C. with decomposition

EXAMPLE 13 (Y: N—; R: —OCH$_3$)

(E)-2-(2-methoxyiminoethyl)-phenoxyacetic acid 2-(2-hydroxyiminoethyl)-phenoxyacetic acid is esterified and methylated by the already described procedure. After saponification and recrystallization from water, the pure (E) isomer is obtained in the form of a white lightly coloured amorphous solid; 850 mg (3.8 mmoles) of (E) isomer are obtained from 3 g (14 mmoles), equivalent to a yield of 27%.

IR (KBr, cm$^{-1}$): 3500/2600, 1740, 1705, 1615/1600, 1500

NMR (CDCl$_3$, istd TMS=0 ppm): outside range (broad, 1H), 8.20 (t, 1H), 7.4/6.9 (4H, m), 4.71 (s, 2H), 4.01 (s, 3H), 3.81 (d, 2H)

Melting point: 135/139° C.

EXAMPLE 14 (Y: N—; R: —OCH$_2$CONH$_2$)

(E)-2-(2-aminocarbonylmethyleneoxyiminoethyl)-phenoxyacetic acid

The method is identical to those already described.

IR (KBr, cm$^{-1}$): 3500, 3250, 3080/2600, 1700, 1650/1630, 1580, 1480

Melting point: 105° C. with decomposition.

D) Reagents of formula (III) in which X is —O—, n is 0 (zero), Y is N—, R is —OCH$_3$, and Z is as specified in the following Examples 15 to 17.

EXAMPLE 15 (Z: 5—OH)

(E)-2-methoxyiminomethyl-5-hydroxy-phenoxyacetic acid

The starting product is 2,4-dihydroxybenzaldehyde. 138 mg of this aldehyde (1.01 mmoles) are suspended in 2 ml of methylene chloride, and 340 mg of dihydropyran (4.0 moles) and 25 mg of pyridinium paratoluenesulphonate are added; the reaction is conducted at 20° C. for 24 hours. The progress of the reaction can be followed by RP18 TLC (eluent methanol\water 7:3). The solvent is removed under vacuum at 40° C., the crude reaction product (2-hydroxy-4-tetrahydropyranoyloxy-benzaldehyde) is dissolved in 1 ml of anhydrous acetonitrile, and 158 mg (1.1 mmoles) of potassium carbonate, 184 mg (1.1 mmoles) of ethyl bromoacetate and 23 mg of TEBA are added. The system is left at 80° C. for 2 hours. It is diluted with 50 ml of ethyl ether and filtered through celite. The filtrate is evaporated under vacuum and the crude product is chromatographed over flash silica (eluent ethyl ether/petroleum ether 1:2). In this manner 244 mg (0.8 mmoles) of pure product are obtained in the form of white amorphous powder. Yield 80%. The structure is confirmed by analysis.

NMR (CDCl$_3$, TMS=0 ppm): 10.39 (s, 1H), 7.83 (d, 1H), 6.76 (dd, 1H), 6.5 (d, 1H), 5.48 (t, 1H), 4.7 (s, 1H), 4.26 (q, 2H), 3.8 (m, 1H), 3.6 (m, 1H), 1.9/1.56 (m, 6H), 1.19 (t, 3H)

Melting point: 65° C.

The ester is saponified by the already described method, crystallizing the acid to pH 2, and the tetrahydropyranoyl group is eliminated (confirmed by NMR). In this manner 2-formyl-4-hydroxy-phenoxyacetic acid is very easily obtained by direct crystallization, and from the crude product (160 mg) the oxime derivative is obtained with NH$_2$OCH$_3$. HCl (30% aqueous solution) by the already described procedure. After decoloration with carbon and alumina, the product is recrystallized twice from water to obtain the (E) isomer in pure form as a white solid of crystalline appearance. 88 mg (0.42 mmoles) are obtained. Yield 42%.

IR (KBr, cm$^{-1}$): 3300/3200, 1705, 1620, 1600

NMR (DMSOd$_6$, TMS=0 ppm): 13.07 (b, 1H), 9.96 (s, 1H), 8.28 (s, 1H), 7.49 (d, 1H), 6.41 (dd, 1H), 6.32 (d, 1H), 4.67 (s, 2H), 3.8 (s, 3H)

Melting point: 120° C.

EXAMPLE 16 (Z: 5-OCOCH$_2$NH$_2$=)

(E)-2-methoxyiminomethyl-5-aminocarbonylmethyleneoxy-phenoxyacetic acid

The desired product is obtained using the aforesaid procedure, by the described alkylation of the hydroxyl in position 5 of the starting oxime as ethyl ester.

NMR (DMSOd$_6$, TMS=0 ppm): 13.1 (b, 1H), 8.27 (s, 1H), 7.51 (d, 1H), 7.35/7.28 (d, broad 2H), 6.42 (dd, 1H), 6.33 (d, 1H), 4.7 (s, 2H), 4.45 (s, 2H), 3.8 (s, 3H)

Melting point: 183°–185° C.

EXAMPLE 17 (Z: 5—OCH$_2$COOBut)

(E)-2-methoxyiminomethyl-5-tert.butyloxycarbonylmethyleneoxy-phenoxyacetic acid

This product is obtained in a manner identical to the aforegoing. Its characteristics are:

IR (KBr, cm$^{-1}$): 3250, 1710, 1650, 1600

NMR (DMSOd$_6$, TMS=0 ppm): 13 (b, 1H), 8.4 (s, 1H), 7.53 (d, 1H), 6.43 (dd, 1H), 6.37 (d, 1H), 4.73 (s, 1H), 4.6 (s, 1H), 1.43 (s, 9H)

Melting point: 190° C.

E) Reagents of formula (III) in which X is —O—, n is 0 (zero), R is —OCH$_3$, Y is N— and Z is as indicated in Examples 18 and 19, these reagents being prepared by procedures identical to those used for the corresponding 4-hydroxy derivatives.

EXAMPLE 18 (Z: 4—OCONH₂)

(E)-2-methoxyiminomethyl-4-aminocarbonyloxy-phenoxyacetic acid

IR (KBr, cm⁻¹): 3500/3200, 1720, 1630, 1500

NMR (DMSO-d₆, istd TMS=0 ppm): 13.2 (b, 1H), 8.28 (s, 1H), 7.6/7.5 (b, 2H), 7.47 (d, 1H), 6.6/6.5 (m, 2H), 4.67 (s, 2H), 3.82 (s, 3H)

Melting point: 189° C.

EXAMPLE 19 (Z: 4—OCH₂COO-t-But)

2-methoxyiminomethyl-4-aminocarbonyloxy-phenoxyacetic acid

IR (KBr, cm⁻¹): 3250, 2980, 1700, 1600, 1510

NMR (DMSO-d₆, istd TMS=0 ppm): 13 (b, 1H), 8.3 (s, 1H), 7.5 (s, 1H), 6.6 (m, 2H), 4.7 (s, 2H), 3.82 (s, 3H), 1.5 (s, 9H)

Melting point: 195° C.

F) Reagents of formula (III) in which X is —O—, Z is 4—NO₂, n is 0 (zero), Y is N— and R is as indicated in Examples 20 and 21.

EXAMPLE 20 (a: —OH)

(E)-4-nitro-2-hydroxyiminomethyl-phenoxyacetic acid

The starting material is 2-hydroxy-4-nitro-benzaldehyde (commercial). It is treated with chloroacetic acid, sodium salt, in accordance with the already described procedure, the derivative (4-nitro-2-formylphenoxyacetic acid) being treated with hydroxylamine by the standard procedure. The corresponding oxime is crystallized from water as a single diastereoisomer, without the need for further purification.

IR (KBr, cm⁻¹): 3600, 3490, 3250/2900, 1720, 1610, 1508

NMR (DMSO): 13.4 (b, 1H), 11.72 (s, 1H), 8.46 (d, 1H), 8.34 (s, 1H), 8.22 (dd, 1H), 7.42 (d, 1H), 4.97 (s, 1H)

Melting point: 193° C.

EXAMPLE 21 (R: —OCH₃)

(E)-2-methoxyiminomethyl-4-nitro-phenoxyacetic acid 2-formyl-4-nitro-phenoxyacetic acid is treated with methoxyamine hydrochloride by the procedure already described for hydroxy oximes. The product is crystallized from water/ethanol (80/20) maintaining the temperature between 30° C. and 35° C. The product (crystalline white powder) is obtained as a single isomer without the need for further purification.

IR (KBr, cm⁻¹): 3550, 3100, 2900, 1730, 1600, 1525

NMR (DMSOd₆): 13.4 (b, 1H), 8.43 (d, 1H), 8.39 (s, 1H), 8.23 (dd, 1H), 7.17 (d, 1. ), 4.78 (s, 2a), 3.95 (s, 1H)

Melting point: 195/198° C.

G) Reagents of formula (III) in which X is —O—, n is 0 (zero), Y is N—, R is —OCH₃ and Z is as specified in Examples 22–24.

EXAMPLE 22 (Z: 4—NH₂)

(E)-2-methoxyiminomethyl-4-amino-phenoxyacetic acid (E)-2-methoxyiminomethyl-4-nitro-phenoxyacetic acid obtained as in the preceding example is reduced as described in the literature (see for example "ORG.SYN" coll. vol. I, 52 and references cited therein). In a typical procedure 14 g (55 mmoles) of 4-nitro derivative are dissolved in 65 ml of 6N ammonia (390 mmoles). 6 g of hydrogen sulphide (176 mmoles) are added and after 5 hours at 40° C. the excess hydrogen sulphide is removed under vacuum at 40/50° C. The system is cooled to 20° C. and the sulphur precipitates and is filtered off. The pH is adjusted to 4 to crystallize the para amino derivative. This is then dissolved at pH 8, decolorized over carbon and recrystallized with hydrochloric acid, adjusting the pH to 3. In this manner 7.3 g (32 mmoles) of the corresponding amino acid are obtained in the form of a clear yellow crystalline powder. Yield 59%.

IR (KBr, cm⁻¹): 3500/3050, 1650, 1850, 1505

NMR (CDCl₃, TMSO=0 ppm): 8.17 (s, 1H), 6.68/7.1 (m, 3H), 4.7 (s, 2H), 3.5 (broad, 3H)

Melting point: 187° C.

EXAMPLE 23

(E)-2-methoxyiminomethyl-4-acetylamino-phenoxyacetic acid

The (E)-2-methoxyiminomethyl-4-amino-phenoxyacetic acid obtained in the preceding example is acetylated as follows:

5 g (21.9 mmoles) are suspended in 30 ml of anhydrous methylene chloride, and 3.05 ml (22 mmoles) of triethylamine (TEA) are added followed by 2.80 ml (22 mmoles) of trimethylchlorosilane (TMCS). The reaction is conducted for 30 minutes at 20° C. The system is cooled to −5° C. and 1.63 ml (23 mmoles) of acetyl chloride and 3.1 ml of TEA are added. The system is left to react at 0° C. for 2 hours, after which it is washed twice with freezing cold water. The product is extracted in water with 150 ml of a saturated sodium bicarbonate solution. The product is crystallized at pH 2 with concentrated hydrochloric acid. The crude product (6 g) is redissolved in 100 ml of water and 2 g of sodium bicarbonate. The solution is decolorized with carbon and after filtration is crystallized at +30° C. by acidifying to pH 2. In this manner 5.7 g (21 moles) of product are obtained as a brown crystalline solid. Yield 96%.

IR (KBr, cm⁻¹): 3500, 3250, 1715, 1700, 1650, 1505

NMR (DMSO, TMS=0 ppm): 8.17 (s, 1H), 7.9 (s, 1H), 6.75/7.2 (m, 3H), 4.7 (s, 2H), 2.2 (s, 3H), outside range (broad, 1H)

Melting point: 155/158° C.

EXAMPLE 24 (Z: 4—NHSO₂CH₃)

(E)-2-methoxyimino-4-mesylamino-phenoxyacetic acid 5 g of the acid of Example 1 are treated in the manner of Example 2 with 1.8 ml (23 mmoles) of mesyl chloride. After treatment 6 g (19.6 mmoles) of product are obtained as straw yellow crystalline powder. Yield 89%.

IR (KBr, cm⁻¹): 3470, 3300/3080, 1713, 1520

NMR (CDCl₃, TMSO=0 ppm): 8.5 (s, 1H deuterable), 8.17 (s, 1H), 6.82/7.25 (m, 3H), 4.71 (s, 2H), 3.5 (s, 3H), outside range 1H deuterable Melting point: 193/195° C.

H) Reagents of formula (III) in which X is —O—, Z is 6—OCH₃, n is 0 (zero), Y is N— and R is as specified in Examples 25 and 26.

EXAMPLE 25 (R: —)H)

(E)-2-hydroxyiminomethyl-6-methoxy-phenoxyacetic acid

The starting product is 2-hydroxy-3-methoxy benzaldehyde, known commonly as o-vanillin. Alkylation is conducted by the already described method, using ethyl bromoacetate under reflux in acetonitrile. In this manner 2-formyl-6-methoxy-phenoxyacetic acid is obtained in the form of the ethyl ester. The oily crude product is saponified to give the corresponding acid in the form of a white crystalline solid. Melting point 118/119° C. NMR (DMSO-d₆): 13 (b, 1H), 10.5 (s, 1H), 7.4/7.1 (m, 3H), 4.8 (s, 2H), 3.85 (s, 3H). IR (KBr, cm⁻¹): 3100/2600, 1735, 1700. This is transformed into the corresponding oxime using hydroxylamine hydrochloride.

The oxime is crystallized from water at 80° C. to selectively produce the (E) oxime. The straw coloured crystalline solid has a diastereoisomeric purity (HPLC) >98%.

IR (KBr, cm⁻¹): 3400/3150, 3080, 2980/2818, 1725, 1496

NMR (DMSO, TMS=0 ppm): 11.26 (s, 1H), 8.3 (s, 1H), 7.35/7.10 (m, 3H), 4.7 (s, 2H), 3.8 (s, 3H), outside range 1H Melting point: 138/139° C.

EXAMPLE 26 (R: —OCH₂CN)

(E)-2-cyanomethyloxyiminomethyl-6-methoxy-phenoxyacetic acid 2-formyl-6-methoxy-phenoxyacetic acid ethyl ester is transformed into oxime with hydroxylamine hydrochloride by the standard procedure. The oily crude product is alkylated with bromoacetonitrile in acetonitrile by the already described method.

The alkylation product is purified by column chromatography (silica gel 60, eluent ethyl ether/methanol 9:1).

In this manner an oily product is obtained which is saponified with sodium hydroxide by the already described procedure, to give the product as a single (E) isomer, of straw white crystalline appearance.

IR 3080/2800, 1715, 1506

NMR (DMSO, TMS=0 ppm): 8.3 (s, 1H), 7.35/7.10 (m, 3H), 4.7 (s, 2H), 4.1 (s, 2H), 3.81 (s, 3H), outside range 1H Melting point: 95/96° C.

PREPARATION OF OXIME DERIVATIVES (I)

The oxime derivatives (I) are prepared by condensing the aforedescribed reagents (III) with cephalosporanic nuclei (II). By way of example, three different condensation methods are described hereinafter. The most important method is that illustrated in Example 28.

The method of Example 27 is useful essentially only for preparing certain derivatives of Examples 1 to 6. The method illustrated in Example is a variant useful for those oxime derivatives having a blocked (protected) acid functional group such as tert.butylester. This method in fact represents a continuation of the process of Example 28.

Finally it should be noted that all nuclei were prepared by processes well known in the patent and scientific literature.

EXAMPLE 27

7-[(E)-2-(methoxyiminomethyl)phenylacetamido]-3-acetyloxymethyl-3-cephem-4-carboxylic acid The general reaction scheme is as follows.

METHOD I:

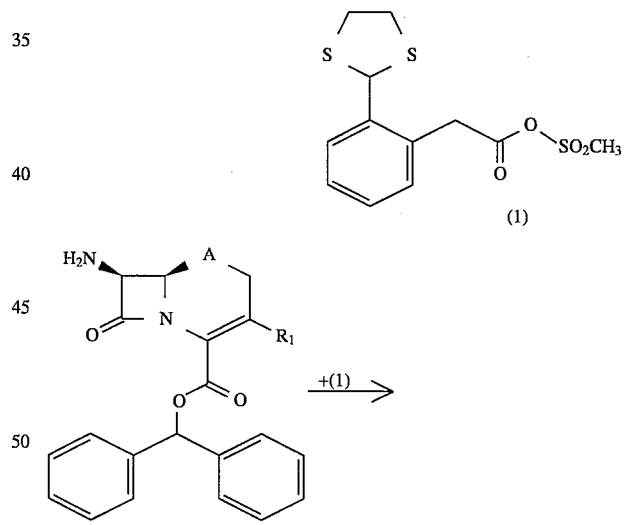

METHOD I:

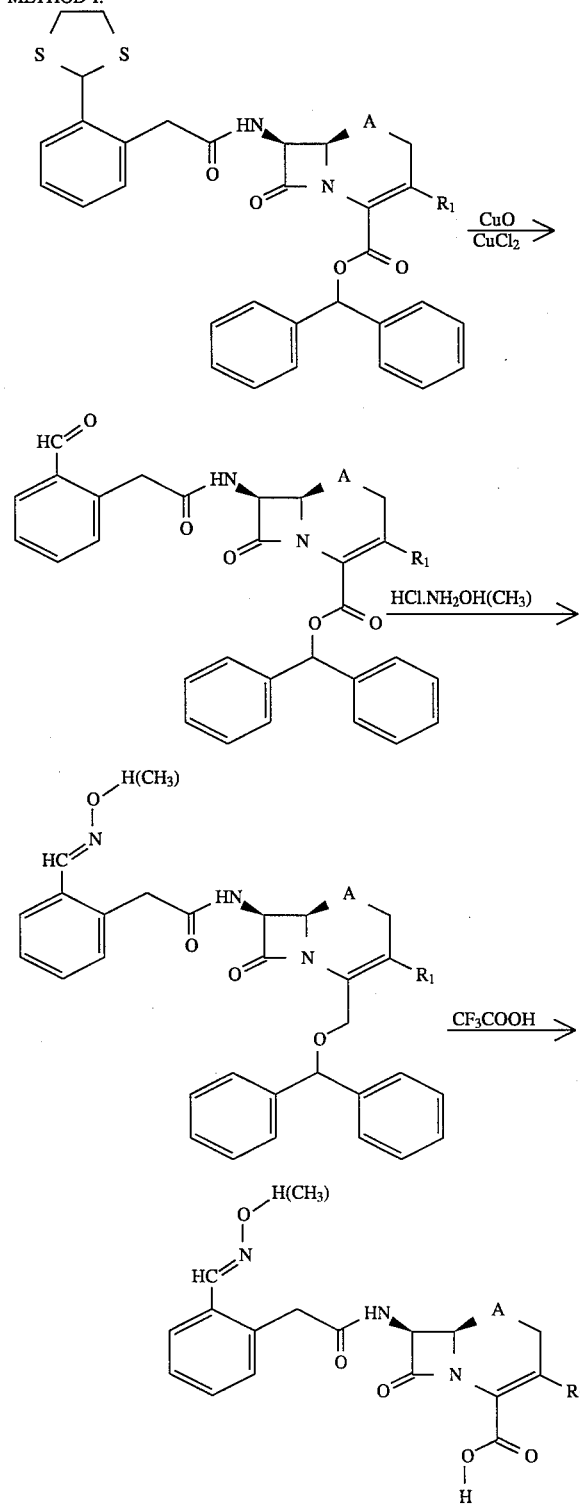

In detail, 0.94 ml (6.7 mmoles) of triethylamine and 0.46 ml (5.9 mmoles) of mesyl chloride are added to a solution of 1 g (4.2 mmoles) of 2-(1,3-dithiolan-2-yl)phenylacetic acid in 10 ml of methylene chloride, cooled to −15° C. The methanesulphonic anhydride methylene solution obtained in this manner is used as such.

The said mixed anhydride solution is added (at −20° C.) to a solution of 7-ACA benzhydrylic ester (3.8 mmoles) in 15 ml of methylene chloride. The system is agitated for 40 minutes after which 20 ml of NaHCO$_3$-saturated water are added followed by water. The phases are separated and the organic part evaporated under vacuum. The residue provides 1.25 g (1.9 mmoles) of 7-[2-(1,3-dithiolan-2-yl)phenylacetamido]-3-acetoxymethyl-3-cephem-4-carboxylic acid benzhydrylic ester.

H NMR (DMSO-d$_6$): 1.95 (s, 3H), 3.3/3.5 (m, 4H), 3.55/3.67 (ABsyst. J=13 Hz, 2H), 3.73/3.75 (ABsyst. J=15 Hz, 2H), 4.64/4.86 (ABsyst. J=15 Hz, 2H), 5.15 (d, 4.5 Hz, 1H), 5.78 (dd, 4.5 Hz, 1H), 6.01 (s, 1H), 7.2/7.8 (m, 14H), 9.22 (brd 8 Hz, 1H).

120 mg of CuO and 400 mg of CuCl$_2$ are added to a solution of 7.92 g (12 moles) of benzhydryl ester prepared as above, in 10 ml of acetone. The system is heated to 50° C. for 1 hour. The insoluble part is filtered off and the filtrate evaporated under vacuum. The residue is taken up with diisopropyl ether to hence obtain 4 g of benzhydryl 7-(2-formylphenylacetamido)-3-acetoxy-methyl-4-carboxylate.

0.31 g (3.7 mmoles) of methoxyamine hydrochloride are added to a solution of 2 g (3.4 mmoles) of ester obtained as above, in 20 ml of ethylacetate. The system is agitated at 20° C. for 30 minutes after which 10 ml of water are added and the pH adjusted to 7 with NaHCO$_3$. The phases are separated and the organic part evaporated under vacuum to give 1.72 g (2.8 mmoles) of 7-[2-(methoxyiminomethyl)phenylacetamido]-3-acetoxymethyl-3-cephem-4-carboxylic acid benzhydrylic ester.

6 ml of trifluoroacetic acid are added to a solution of 3.2 moles of ester prepared as above in 10 ml of anisole at 20° C. over a period of 30 minutes, after which 20 ml of diisopropyl ester are added. The precipitate is filtered off and suspended in 50 ml of diisopropyl ester. In this manner 800 ml (1.8 mmoles) of 7-[2-(methoxyiminomethyl)phenylacetamido]-3-acetoxymethyl-3-cephem-4-carboxylic acid are obtained.

IR (KBr pellets, cm$^{-1}$):3500/3279, 1767 (β-lactam), 1680, 1660, 1600, 1535

NMR (DMSO-d$_6$ istd TMS=0 ppm): 2.00 (3H, s), 3.27/3.51 (2H, ABsyst. J=13 Hz), 3.90 (3H, s), 4.72/4.95 (2H, ABsyst. J=15 Hz), 5.00 (1H, d, J=5 Hz), 5.53 (1H, dd, 5 Hz), 8.52 (1H, s), 8.68 (1H, d, J=8 Hz)

Melting point: about 180° C. with decomposition.

EXAMPLE 28

7-[(E)-2-(methoxyiminomethyl)phenoxyacetamido]-3-acetoxymethyl-3-cephem-4-carboxylic acid The general reaction scheme is as follows:

METHOD II

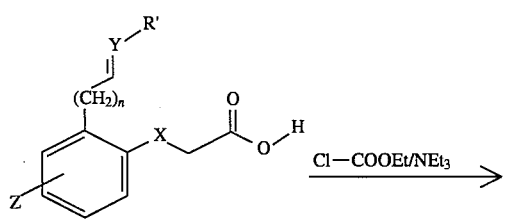

-continued
METHOD II

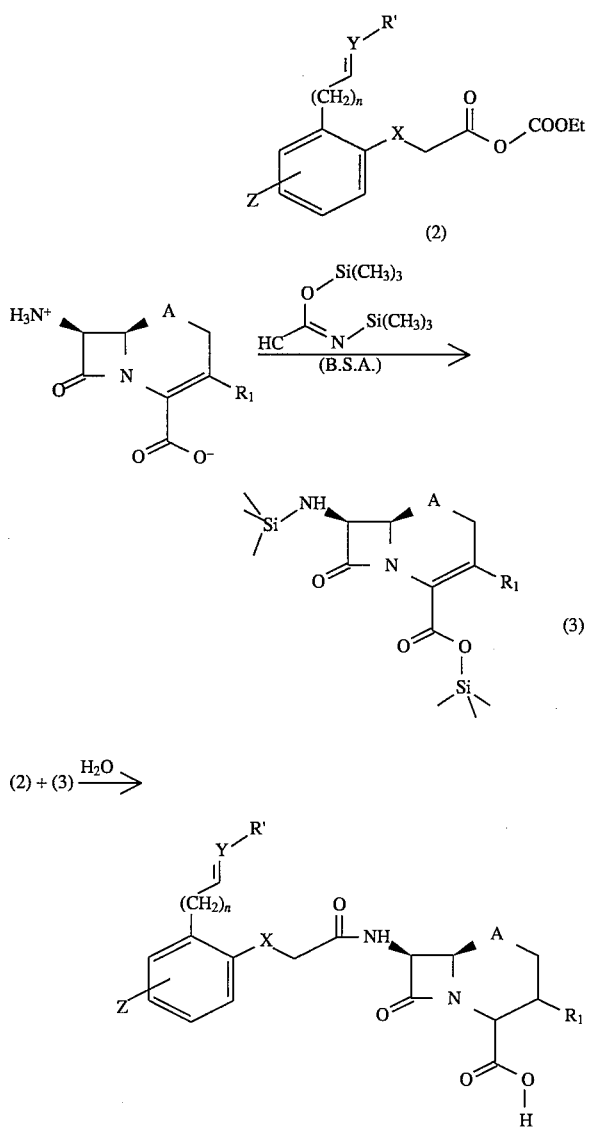

In detail, 8.4 g (31 mmoles) of 7-aminocephalosporanic acid (7-ACA) are suspended in 70 ml of anhydrous methylene chloride. 8.3 ml (34 mmoles) of bis-trimethylsilylacetamide (BSA) are added, the system is heated under reflux until complete dissolution, it is then cooled to −10° C. and the solution of 7-ACA silyl-derivative is then ready for the condensation reaction. Separately, 5 g (24 mmoles) of (E)-2-methoxyiminomethyl phenoxyacetic acid are suspended in 50 ml of methylene chloride and salified with 3.3 ml of triethylamine (TEA).

When dissolution is complete, the system is cooled to −60° C., 50 μl of N-methylmorpholine are added followed by 2.3 ml (24 mmoles) of ethylchloroformate.

It is left to react for 1 hour at −30° C. The silylated 7-ACA solution is bubbled into the mixed anhydride solution and left at 0° C. for 3 hours. The progress of the reaction can be monitored by HPLC: eluent 350 ml methanol, 750 ml water/300 mg $Na_2HPO_4$/200 mg $K_2PO_4$; column LICROSPHER RP8 select B; 260 nm 45° C.; flow 1 ml/min (7-ACA rt 2.2 min condensation product rt 27.6 min). The system is then washed twice with ice cold water, extracted with 100 ml of 1N dilute hydrochloric acid (to eliminate the unreacted 7-ACA) and further washed with water. The methylene phase is evaporated under vacuum until a solid residue is obtained. It is taken up in 200 ml of anhydrous isopropanol, and at 30° C. 4 g of sodium ethylhexanoate dissolved in 100 ml of isopropanol are bubbled in. The system is left to crystallize for 2 hours at 30° C., cooled with an ice and salt bath and filtered under vacuum. After drying, 9.1 g of product are obtained in the form of the sodium salt. The molar yield is 78%. On NMR analysis there seems to be a single isomer with E configuration, as was the starting acid. The synthesis therefore does not result in loss of stereochemistry.

IR (KBr, $cm^{-1}$): 3500/3279, 1767 (β-lactam), 1686, 1664

NMR (DMSO-$d_6$ TMS=0 ppm): 9.0 (d, 1H), 8.45 (s, 1H), 7.0/7.7 (m, 4H), 5.55 (dd, 1H), 5.0 (d, 1H), 5.0/4.75 (ABsyst. 2H), 4.7 (s, 2H), 3.9 (s, 3H), 3.45/3.15 (ABsyst. 2H), 2.0 (s, 3H)

Melting point: 175° C. with decomposition.

In an identical manner to Example 28, the oxime derivatives of formula (I) were prepared in which X is absent, Y is N—, Z is —H and n is 0 (zero), the values of A, R and $R_1$ being as shown in Table 1 below, to the side of each Example from 29 to 32.

TABLE 1

| Ex. No. | R | $R_1$ | A | M.P. °C. | NMR ppm (DMSO $d_6$ TMSO = 0) IR $cm^{-1}$ (KBr) |
|---|---|---|---|---|---|
| 29 | —$OCH_3$ | —$OCH_3$ | S | 174 | 12,6 1H(b); 9,0 1H(d); 8,4 1H(s); 7,7/7,2 4H(m); 5,4 1H(dd); 5,1 1H(d); 3,9 3H(s); 3,75 3H(s); 3,7 2H(s); 3,68/3,58 2H(ABsytstem). 1765(beta-lactam); Acid Form |
| 30 | —$OCH_3$ | —Cl | $CH_2$ | 223 | 8,9 1H(d); 8,45 1H(s); 7,7/7,2 4H(m); 5,1 1H(dd); 3,9 3H(s); 3,7 2H(s); 3,66 1H(m); 2,49 2H(m); 2,3 1H(m); 1,7 1H(m) 1750(beta-lactam); Sodium salt |
| 31 | —$OCH_3$ | \-$CH_2$-S-[N—N heterocycle with N-$CH_3$] | S | 120 | 9,1 1H(d); 8,45 1H(s); 7,2/7,7 4H(m); 5,65 1H(dd); 5,05 1H(d); 4,26/4,35 2H(ABsystem); 3,95 3H(s); 3,85 3H(s); 3,7 2H(s); 3,6/3,3 2H(ABsystem) 1759(beta-lactam); Sodium salt |
| 32 | —$OCH_3$ | —Cl | S | 180 | 12,6 1H(b); 9,0 1H(d); 8,4 1H(s); 7,7/7,2 |

TABLE 1-continued

| Ex. No. | R | R₁ | A | M.P. °C. | NMR ppm (DMSO d₆ TMSO = 0) IR cm⁻¹ (KBr) |
|---------|---|----|----|----------|-------------------------------------------|
|         |   |    |   |          | 4H(m); 5,8 1H(dd); 5,2 1H(d); 4,0/3,6 2H (ABsystem) 3,7 2H(s); 3,85 3H(s). 1750(beta-lactam); Acid form |

In the same manner the oxime derivatives of formula (I) were prepared as shown in the following Table 2, in which X is —O—, Y is N—, n is 0 (zero) and Z, R and R₁ have the meanings specified in each of the Examples from 33 to 53.

TABLE 2

| EX. No. | Z | R | R₁ | A | M.P. °C. | NMR ppm (DMSO d₆ TMSO = 0) IR cm⁻¹ (KBr) |
|---------|---|---|----|----|---------|-------------------------------------------|
| 33 | H | OCH₃ | CH₂OCOCH₃ | S | 175 | 9,0 1H(d); 8,45 1H(s); 7,7/7,0 4H(m); 5,55 1H(dd); 5,0 1H(d); 5,0/4,75 2H(ABsystem); 4,72 2H(s); 3,9 3H(s); 3,45/3,15 2H(ABsystem); 2,0 3H(s) 1767(beta-lactam); Sodium salt |
| 34 | H | OCH₃ | CH₂OCOCH₃ | O | 163 | 9,1 1H(d); 8,45 1H(s) 7,7/7,0 4H(m); 5,65(dd); 5,22 1H(d); 5,1/4,82 2H(ABsystem); 4,7 2H(s); 3,9 3H(s); 3,60/3,20 2H(ABsystem); 2,0 3H(s) 1769(beta-lactam); Sodium salt |
| 35 | 4-NH₂ | OCH₃ | -CH₂-S-(5-methyl-1,3,4-thiadiazol-2-yl) | S | 197 | 9,1 1H(d); 8,15 1H(s); 6,7/7,2 3H(m); 5,6 1H(dd); 5,0 1H(d); 4,7 2H(s); 4,5/4,37 2H(ABsystem); 3,85 3H(s); 3,63/3,37 2H(AB); 2,65 3H(s) 1763(beta-lactam); Acid form |
| 36 | H | OH | -CH₂-S-(1-methyl-1H-tetrazol-5-yl) | S | 147 | 11,27 1H(s); 9,1 1H(d); 8,27 1H(s); 7,68/7,26 4H(m); 5,65 1H(dd); 5,05 1H(d); 4,35/2,25 2H(AB); 3,90 3H(s); 3,80 3H(s); 4,7 2H(s); 3,6/3,3 2H(AB) 1756(beta-lactam); Sodium salt |
| 37 | H | OH | Cl | S | 160/170 dec.* | 11,25 1H(s); 8,25 1H(s); 7,68/7,26 4H(m); 5,8 1H(dd); 5,2 1H(d); 4,0/3,6 2H(AB); 4,72 2H(s); 3,8 3H(s); 13,2 1H(b); 9,1 1H(d); 1753(beta-lactam); Acid form |
| 38 | 4-NO₂ | OH | -CH₂-S-(5-methyl-1,3,4-thiadiazol-2-yl) | S | 195 | 13,2(b, 1H); 11,7(1H, s); 9,05 (1H d); 8,46/8,21(m, 3H); 7,24 (d, 1H); 5,6(dd, 1H); 5,1(d, 1H); 4,96(s, 2H); 4,45(AB, 2H); 3,5(AB, 2H); 2,65(s, 3H) 1758(beta-lactam); Acid form |
| 39 | 6-OCH₃ | OH | -CH₂-S-(1-methyl-1H-tetrazol-5-yl) | S | 162 | 10,85(1H, s); 9,2(1H, d); 8,2 (1H,s); 7,3/7,0(m, 3H); 5,7 (1H, dd); 5,1(d, 1H); 4,7(s, 2H); 4,4/4,2(2H, AB); 3,9(3H, s); 3,82(3H, s); 3,7/3,6(2H, AB) 1753(beta-lactam); Sodium salt |
| 40 | 6-OCH₃ | OCH₂CONH₂ | -CH₂-S-(1-methyl-1H-tetrazol-5-yl) | S | 149 | 9,2(1H, d); 8,5(1H, s); 7,35/7,0(m, 5H); 5,7(1H, dd); 5,1(1H, d); 4,7(2H, s); 4,5 (2H, s); 4,3(2H, AB); 3,95(3H, s); 3,82(3H, s); 3,7(2H, AB); 1753; beta-lactam); Sodium salt. |

5,574,153

TABLE 2-continued

| EX. No. | Z | R | R₁ | A | M.P. °C. | NMR ppm (DMSO d₆ TMSO = 0) IR cm⁻¹ (KBr) |
|---|---|---|---|---|---|---|
| 41 | H | OCH₂CONH₂ | 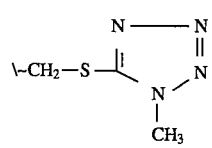 | S | 110 dec₄* | 9,2(1H, d); 8,16(1H, s); 7,65 (1H, dd); 7,4(1H, m); 7,28(2H, dd); 6,9/7,0(2H, m); 5,7(1H, dd); 5,1(1H, d); 4,7(2H, s); 4,45(2H, s); 4,3/4,4 (2H, AB); 3,95(s, 3H); 3,8/3,6 (2H, s) 1770(beta-lactam); Acid form |
| 42 | H | OCH₃ | Cl | CH₂ | 104 dec.* | 9,0(1H, d); 8,5(1H, s); 7,7/6,9(4H, m); 5,2(1H, dd); 4,7/4,65(2H, AB); 3,85(s, 3H),; 3,7(1H, m); 2,45(2H, m); 2,25(1H, m); 1,8(1H, m) 1755(beta-lactam); Sodium salt |
| 43 | H | OCH₃ | 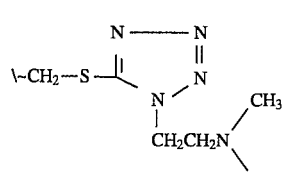 | S | 110° dec.* | 8,95(1H, d); 8,45(1H, s); 7,7/6,95(1H, m); 5,5(1H, dd); 4,95(1H, d); 4,7(2H, s); 4,35 (2H, t); 4,4/4,2(2H, AB); 3,9 (3H, s); 3,9/3,35(2H, AB); 2,7 (2H, t); 2,15(6H, s) 1763(beta-lactam); sodium salt |
| 44 | H | OCH₃ | OCH₃ | S | 120 | 9,0(1H, d); 8,5(1H, s); 7,7/7,0(4H, m); 5,45(1H, dd); 4,95(1H, d); 4,7(2H, s); 3,9 (3H, s); 3,6(3H, s); 3,45/3,3 (2H, AB) 1759(beta-lactam); Sodium salt |
| 45 | H | OCH₃ | 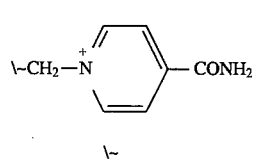 | S | 149 dec.* | 9,6(2H, d); 9,2(1H, d); 8,9 (1H, b); 8,5(2H, d); 8,2(1H, b); 7,7/7,0(4H, m); 5,8/5,2 (2H, AB); 5,5(1H,dd); 5(1H, d); 4,7(2H, s); 3,65(3H, s); 3,55/3,1(2H, AB); 1760(beta-lactam); Inner salt |
| 46 | 5-OH | OCH₃ | 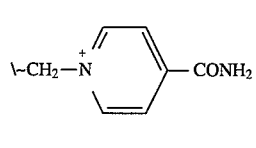 | S | 112 dec.* | 9,95(1H, b); 9,6(2H, d); 9,2 (1H, d); 8,9(1H, b); 8,5(2H, d); 8,3(1H, b); 8,2(1H, s); 7,5(1H, d); 6,5/6,3(2H, m); 5,8/5,2(2H, AB); 5,6(1H, dd); 5(1H, d); 4,7(2H, s); 3,83 (3H, s); 3,5/3,1(2H, AB); 1760(beta-lactam); Sodium salt |
| 47 | 5-OH | OCH₃ | CH₃ | S | 171 | 13,07(1H, b); 9,96(1H, s); 9,2 (1H, d); 8,28(1H, s); 7,5(1H, d); 6,43(1H, s); 6,32(1H, s); 5,7(1H, dd); 5,1(1H, d); 4,67 (2H, s) 3,82(3H, s); 3,4/3,2 (2H, AB) 2,0(3H, s); 1750(beta-lactam); sodium salt |
| 48 | H | OCH₂CONH₂ | Cl | S | 154 | 9,2(1H, d); 8,6(1H, s); 7,7 (1H, d); 7,4/6,9(5H, m); 5,75 (1H, dd); 5,1(1H, d); 4,7(2H, s); 4,5(2H, s); 3,8/3,6(2H, AB); 1800(beta-lactam); Acid form |
| 49 | 5-OH | OCH₃ | 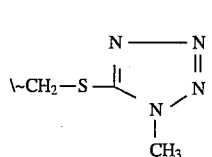 | S | 189 | 13,1(1H, b); 9,9(1H, s); 9,2 (1H, d); 8,3(1H, s); 7,5/6,3 (3H, m); 5,7(1H, dd); 5,15(1H, d); 4,67(2H, s); 4,4/4,2(2H, AB); 3,9(3H, s); 3,83(3H, s); 3,8/3,6(2H, AB) 1761(beta-lactam); Acid form |

TABLE 2-continued

| EX. No. | Z | R | $R_1$ | A | M.P. °C. | NMR ppm (DMSO $d_6$ TMSO = 0) IR $cm^{-1}$ (KBr) |
|---|---|---|---|---|---|---|
| 50 | 5-$OCH_2CONH_2$ | $OCH_3$ | \-$CH_2$-S-[1-methyl-tetrazol-5-yl] | S | 136 dec.* | 9,17(1H, d); 8,3(1H, s); 7,5/6,3(5H, m); 5,3(1H, dd); 5,1(1H, d); 4,7(2H, s); 4,5 (2H, s); 4,4/4,2(2H, AB); 3,92 (3H, s); 3,82(3H, s); 3,8/3,6 (2H, AB) 1755(beta-lactam); Sodium salt |
| 51 | 4-OH | $OCH_3$ | \-$CH_2$-S-[1-methyl-tetrazol-5-yl] | S | 194 | 13,07(1H, b); 10(1H, s); 8,3 (1H, s); 7,5/6,3(3H, m); 5,3 (1H, dd); 5,1(1H, d); 4,67(2H, s); 4,4/4,2(2H, AB); 3,94(3H, s); 3,82(3H, s); 3,8/3,6(2H, AB) 1760(beta-lactam); Acid form |
| 52 | 4-$OCH_2CONH_2$ | $OCH_3$ | \-$CH_2$-S-[1-methyl-tetrazol-5-yl] | S | 198 | 13,07(1H, b); 9,2(1H, d) 8,3 (1H, s); 7,5/6,5(5H, m); 5,3 (1H, dd); 5,15(1H, d); 4,7(2H, s); 4,5(2H, s); 4,4/4,2(2H, AB); 3,92(3H, s); 3,84(3H, s); 3,8/3,6(2H, AB); 1763(beta-lactam); Acid form |
| 53 | 6-$OCH_3$ | $OCH_2CONH_2$ | —H | S | 145 | 13(1H, b); 9,0(1H, d); 8,55 (1H, s); 7,4/7,1(3H, m); 5,8 (1H, dd); 5,12(1H, d); 6,52 (1H, m); 4,8(2H, s); 4,5(2H, s); 3,9(3H, s); 3,6/3,4(2H, m) 1770(beta-lactam); Acid form |

*"dec." means "with decomposition"

EXAMPLE 54

7-[(E)-2-(carboxymethyleneoxyimino-methyl)phenoxyacetamido]-3-(1-methyl-1,2,3,4-tetrazol-5-yl)thiomethyl-4-carboxylic acid The general reaction scheme is as follows:

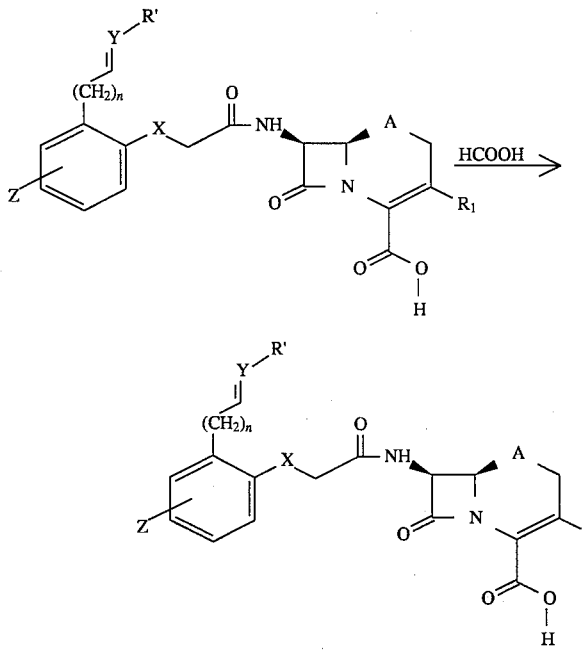

where R' and/or Z=$OCH_2COO$-tBut
where R' and/or Z=$OCH_2COOH$

In detail (the method is initially identical to that illustrated in Example 28), 15 g of 7-amino-3-(1-methyl-1,2,3,4-tetrazol-5-yl)thiomethyl-4-cephalosporanic acid (45 mmoles) are silylated in methylene chloride with 12 ml (49 mmoles) of BSA. Simultaneously the mixed anhydride is prepared using 12.5 g (40 mmoles) of (E)-2-(tert.butoxycarbonyloxymethyleneoxyiminomethyl)phenoxyacetic acid salified with 5.5 ml of TEA and reacted with 4 ml (40 mmoles) of ethyl chloroformate, using 100 µl of N-methylmorpholine as catalyst. The procedure, times and method used in the preparation and condensation are perfectly superimposable. The reaction can be monitored with the same HPLC system.

On termination of the synthesis the described washes are carried out, the methylene is evaporated to residue, but 70 ml of absolute formic acid are added instead of the isopropanol used for crystallizing the product. This releases the t-butyl ester. It is left to react at ambient temperature for about 4 hours. It is taken up in 200 ml of toluene and the toluene/formic acid azeotrope distilled under vacuum. The residue is taken up in 100 ml of anhydrous isopropanol and 15 g of sodium ethyl hexanoate dissolved in 100 ml of isopropanol added. It is left to crystallize overnight at 0° C. The precipitate is filtered off, washed with cold isopropanol and dried to give 15 g of product in the form of the bisodium salt (confirmed by acidimetric titration). The yield is 58.6%.

IR (KBr, $cm^{-1}$): 1760 (β-lactam)

NMR (DMSO-$d_6$ istd TMS): 9.2 (1H, d), 8.5 (1H, s), 7.65/7.0 (4H, m), 5.7 (dd, 1H), 5.1 (1H, d), 4.78 (2H, s), 4.65 (2H, s), 4.4/4.3 (2H, AB), 3.9 (3H, s), 3.75/3.6 (2H, AB)

Melting point: 205° C.

In the same manner the oxime derivatives of formula (I) illustrated in the following Table 3 were prepared, in which X is —O—, Y is N—, n is 0 (zero) and Z, R, $R_1$ and A have the meanings specified to the side of each of the Examples from 55 to 62.

TABLE 3

| EX. No. | Z | R | R₁ | A | M.P. °C. | NMR ppm (DMSO d₆ TMSO = 0 ppm) IR cm⁻¹ (KBr) |
|---|---|---|---|---|---|---|
| 55 | 6-OCH₃ | OCH₂COOH | H | S | 201 dec.* | >13(2H, b); 9,1(1H, d); 8,55 (1H, s); 7,4/7,1(3H, m); 6,52(1H, m); 5,8(1H, dd); 5,1(1H, d); 4,78(2H, s); 4,65(2H, s); 3,9(3H, s); 3,6/3,4(2H, m) 1755(beta-lactam); Acid form |
| 56 | 5-OH | OCH₂COOH | OCH₃ | S | 165 dec.* | 13(2H, b); 9,95(1H, s); 9,1 (1H, d); 8,3(1H, s); 7,5/6,3 (3H, m); 5,8(1H, dd); 5,15 (1H, d); 4,8(2H, s); 4,65 (2H, s); 3,75(3H, s); 3,68/3,58(2H, AB) 1700(beta-lactam); Acid form |
| 57 | 4-NO₂ | OCH₂COOH | \-CH₂-S-[triazole ring with N-CH₂CH₂N(CH₃)₂] | S | 220 dec.* | 9,2(1H, d); 8,43(1H, d); 8,39(1H, s); 8,22(1H, dd); 7,18(1H, d); 5,81(1H, dd); 5,17(1H, d); 4,77(2H, s); 4,65(2H, s); 4,4/4,3(4H, m); 3,6/3,5(2H, AB); 2,7(2H, t); 2,1(6H, s) 1769 cm⁻¹ (beta-lactam); Sodium salt |
| 58 | 4NH₂ | OCH₂COOH | \-CH₂-S-[triazole ring with N-CH₃] | S | 180 | 9,0(1H, d); 8,17(1H, d); 7,2/6,7(m, 3H); 5,7(1H, dd); 5,15(1H, d); 4,7(2H, s); 4,6 (2H, s); 4,35(2H, AB); 3,95 (3H, s); 3,7(2H, AB) 1701(beta-lactam); Inner salt |
| 59 | H | OCH₂COOH | \-CH₂-S-[triazole ring with N-CH₃] | S | 135 | 9,0(1H, d); 8,45(1H, d); 7,7/6,9(4H, m); 4,65(2H, s); 4,6(2H, s); 4,4/4,2(2H, AB); 3,95(3H, s); 3,6/3,4(2H, AB) 1763(beta-lactam); Sodium salt |
| 60 | 4-NH₂ | OCH₂COOH | \-H₂C-S-[thiadiazole ring with CH₃] | S | 115 | 13,02 1H(b); 9 1H(d); 8,17 1H(s); 7,2/7,6 3H(m); 4,6 2H(s); 4,5/4,4 2H(AB); 3,9 3H(s); 3,7/3,6 2H(AB); 3,45 3H(b); 2,7 3H(s). 1765 cm⁻¹ (beta-lactam); Inner Salt |
| 61 | 4-NO₂ | OCH₂COOH | \-H₂C-S-[triazole ring with N-CH₃] | S | 127 | 9,2 1H(d); 8,46 1H(d); 8,34 1H(s); 8,22 1H(dd); 7,24 1H(d); 5,85 1H(dd); 5,2 1H(d); 4,97 2H(s); 4,68 2H(s); 4,21 2H(AB); 3,62 3H(s); 3,29 2H(AB). 1770 cm⁻¹ (beta lactam); Sodium salt |
| 62 | H | OCH₂COOH | Cl | S | 193 | 13,4 2H(b); 9,1 1H(d); 8,4 1H(s); 7,7/6,9 4H(m); 5,5 1H(dd); 5,1 1H(d); 4,7 2H(s); 4,6 2H(s); 3,8/3,3 2H(AB). 1769 cm⁻¹ (beta lactam); Acid form. |

*"dec." means "with decomposition"

The following Table 4 shows data relative to M.I.C. tests conducted on certain GRAM+ and GRAM− bacterial strains. Even as initial screening, these values give an indication of the potentiality of these new β-lactam antibiotics. For simplicity the data relate to some of the products cited in the examples.

TABLE 4

| MICROORGANISM | 31 | 36 | 38 | 41 | 43 | 49 | 50 | 54 | 58 | 60 |
|---|---|---|---|---|---|---|---|---|---|---|
| GRAM + | | | | | | | | | | |
| staphylococcus aureus ATCC 6538 | 0.031 | 0.063 | 0.031 | 0.063 | 0.063 | 0.031 | 0.016 | 0.25 | 0.25 | 0.016 |
| staphylococcus aureus F2 ISF 3 | 32.00 | 32.00 | 16 | 32 | 120 | 8 | 2 | 128 | 8 | 8 |
| staphylococcus epidermidis. HCF BersetC | 0.125 | 0.25 | 0.063 | 0.125 | 0.250 | 0.031 | 0.031 | 1 | 0.250 | 0.031 |
| staphylococcus epider. CHPL A2 | 2.000 | 2.000 | 1 | 128 | 4.000 | 1 | 0.5 | 8 | 0.5 | 8 |
| Streptococcus feacalis LEP Br | 32.00 | 128 | 32 | 0.402 | 120 | 0.25 | 0.102 | 128 | 0.25 | 0.25 |
| GRAM − | | | | | | | | | | |
| Escherichia coli ATCC 8739 | 32.00 | 4 | 8 | 4 | 2 | 2 | 0.25 | 16 | 2 | 4 |
| Escherichia coli ISF 432 | 4.000 | 4 | 16 | 4 | 4 | 2 | 0.5 | 4 | 4 | 4 |
| Escherichia coli R + TEM ISF 10 | 100 | 100 | 100 | 100 | 100 | 100 | 32 | 100 | 16 | 32 |
| Proteus vulgaris CNUR 6 | 100 | 100 | 100 | 100 | 100 | 100 | 100 | 100 | 100 | 100 |
| Klebsiella pneumonie ATCC 10031 | 4 | 2 | 8 | 4 | 4 | 2 | 0.25 | 4 | 2 | 6 |
| Shighella enteritidis | >128 | 128 | >128 | 128 | 128 | 16 | 16 | 6 | 2 | 6 |

We claim:

1. An oxime compound having antibacterial activity and having the formula (I):

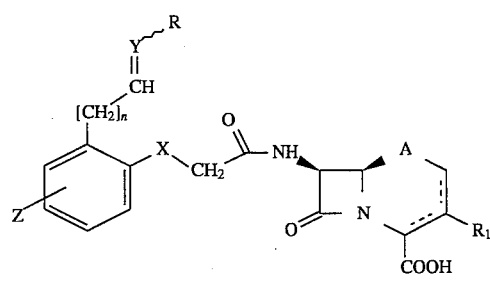

wherein:

X is a direct bond, —O—, —S—, —SO— or $SO_2$;

Y is =N—;

Z is —H, —halogen, —OH, $C_1$–$C_5$ O-alkyl, —$OCH_2CONH_2$, $OCONH_2$, —$OSO_2NH_2$, —$OCH_2CN$, —$NH_2$ either unsubstituted or substituted with $C_1$–$C_6$ alkyl, —$NHCOCH_3$, —$HNSO_2CH_3$,

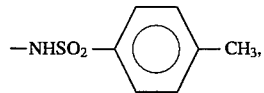

amides of $C_1$–$C_4$ linear acids, amides of benzene and toluene, —$NO_2$, —NO, —CHO, —$CH_2OH$, —COOH, —SH, —SOH, —$SO_2H$, —$SO_3H$, $C_1$–$C_3$ S-alkyl or —$CF_3$;

R is —OH, $C_1$–$C_5$ O-alkyl which is unsubstituted or substituted by halogen, —$OCH_2CH_2NH_2$, —$OCH_2CH_2NH$—$CH_3$, —$OCH_2$(o-, m- or p-) pyridinyl, —$OCH_2CN$, —$OCH_2CONH_2$ or —$OCH_2SO_2NH_2$;

n is a value of 0 to 4;

A is —S—, —SO— or —$SO_2$—;

$R_1$ is —H, —Cl, —$OCH_3$, —$CH_2OCH_2NH_2$, —$CH_2OCH_3$, —$CH_3$, —CH=CH—$CH_3$, —$CF_3$, —$CO_2R_2$ or —$SO_2R_2$, where $R_2$ is alkyl or aryl,

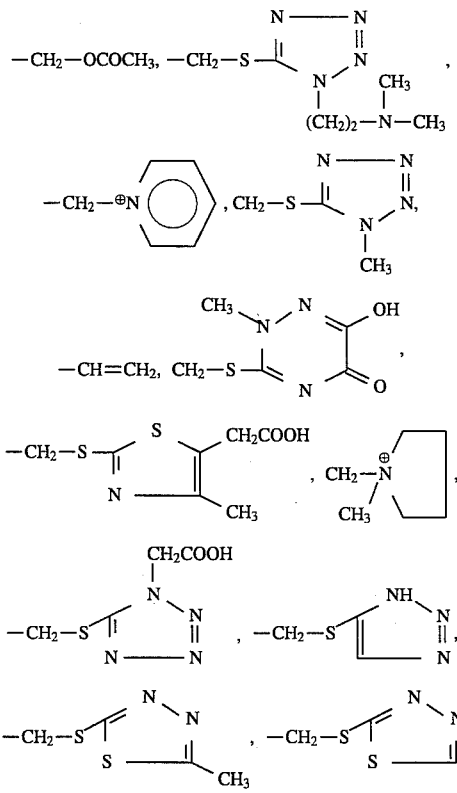

or pharmaceutically acceptable salts thereof or $C_6$- or $C_7$-epimers thereof.

2. The oxime compound of claim 1, which is 7-((E)-2-(methoxyiminomethyl)phenylacetamido)-3-acetyloxymethyl-3-cephem-4-carboxylic acid.

3. The oxime comound of claim 1, which is 7-((E)-2-(methoxyiminomethyl)phenoxyacetamido)-3-acetoxymethyl-3-cephem-4-carboxylic acid.

4. The oxime compound of claim 1, wherein Z is —H and n is O.

5. The oxime compound of claim 1, which is 7-((E)-2-(carboxymethyleneoxyiminomethyl)phenoxyacetamido)3-(1-methyl-1,2,3,4-tetrazol-5-yl) thiomethyl-4-carboxylic acid.

6. The oxime compound of claim 1, which is selected from the group consisting of compounds of the formula (I), wherein X is a direct bond, Z is hydrogen, Y is =N—, n is O, R is —OCH₃, R₁ is —OCH₃ and A is —S—; X is a direct bond, Z is hydrogen, Y is =N—, n is O, R is —OCH₃; R₁ is

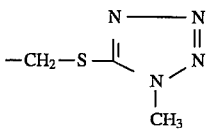

and A is —S—;
X is a direct bond, Z is hydrogen, Y is =N—, n is O, R is —OCH₃; R₁ is —Cl and A is —S—;
X is —O—, Z is 4—NH₂, Y is =N—, n is O, R is OCH₃, R₁ is

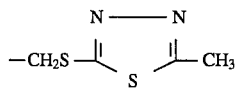

and A is —S—;
X is —O—, Z is hydrogen, Y is =N—, n is O, R is —OH, R₁ is

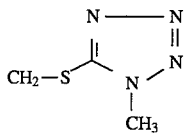

and A is —S—;
X is —O—, Z is hydrogen, Y is =N—, n is O, R is —OH, R₂ is —Cl and A is —S—;
X is —O—, Z is 4 —NO₂, Y is =N—, n is O, R is —OH, R₂ is

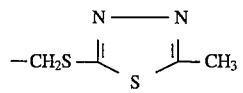

and A is —S—;
X is —O—, Z is 6 —OCH₃, Y is =N—, n is O, R is —OH, R₂ is

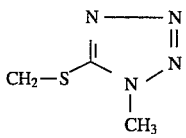

and A is —S—;
X is —O—, Z is 6 - OCH₃, Y is =N—, n is O, R is —OCH₂CONH₂, R₂ is

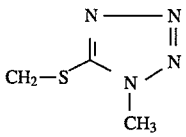

and A is —S—; and
X is —O—, Z is hydrogen, Y is =N—, n is O, R is OCH₂CONH₂, R₂ is

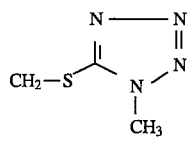

and A is —S—.

7. The oxime compound of claim 1, which is selected from the group consisting of compounds of the formula (I), wherein
X is —O—, Z is 6—OCH₃, Y is =N—, n is O, R is —OCH₂CO₂H, R₁ is hydrogen and A is —S—;
X is —O—, Z is 5—OH, Y is =N—, n is O, R is —OCH₂CO₂H, R₁ is —OCH₃ and A is —S—:
X is —O—, Z is 4 —NO₂, Y is =N—, n is O, R is OCH₂CO₂H, R₁ is

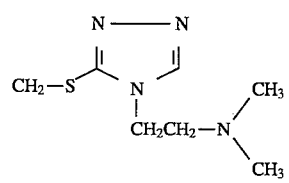

and A is —S—;
X is —O—, Z is 4—NH₂, Y is =N—, n is O, R is —OCH₂CH₂H, R₁ is

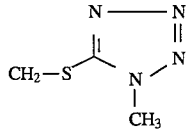

and A is —S—;
X is —O—, Z is hydrogen, Y is =N—, n is O, R is —OCH₂CO₂H, R₁ is

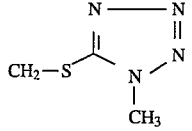

and A is —S—;
X is —O—, Z is 4—NH₂, Y is =N—, n is O, R is —OCH₂CO₂H, R₂ is

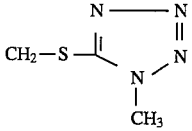

and A is —S—; and
X is —O—, Z is 4 —NO₂, Y is =N—, n is O, R is —OCH₂CO₂H, R₂ is

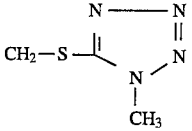

and A is —S—; and
X is —O—, Z is hydrogen, Y is =N—, n is O, R is OCH₂CO₂H, R₂ is C₁ and A is —S—.

* * * * *